US005856186A

United States Patent [19]
Rodan et al.

[11] Patent Number: 5,856,186
[45] Date of Patent: Jan. 5, 1999

[54] METHOD FOR PRODUCING A HIGHLY ENRICHED POPULATION OF OSTEOCLAST CELLS

[75] Inventors: Sevgi B. Rodan, Bryn Mawr; Gregg Wesolowski, Lansdale; Gideon A. Rodan, Bryn Mawr, all of Pa.

[73] Assignee: Merck & Co., Inc., Rahway, N.J.

[21] Appl. No.: 862,556

[22] Filed: May 23, 1997

Related U.S. Application Data

[63] Continuation of Ser. No. 419,210, Apr. 10, 1995, Pat. No. 5,719,058.
[51] Int. Cl.$^6$ .............................. C12N 5/00; C12N 5/02
[52] U.S. Cl. ..................... 435/372; 435/325; 435/366; 435/372; 435/373; 435/378; 435/383
[58] Field of Search ..................................... 435/325, 366, 435/372, 373, 378, 383

[56] References Cited

U.S. PATENT DOCUMENTS

| | | | |
|---|---|---|---|
| 5,073,114 | 12/1991 | Detsch | 433/228.1 |
| 5,168,050 | 12/1992 | Hammonds, Jr. et al. | |
| 5,169,837 | 12/1992 | Largarde et al. | |
| 5,258,494 | 11/1993 | Oppermann et al. | |
| 5,324,819 | 6/1994 | Oppermann et al. | |
| 5,399,493 | 3/1995 | Emerson et al. | |
| 5,403,825 | 4/1995 | Lagarde et al. | |
| 5,405,772 | 4/1995 | Ponting | |
| 5,437,994 | 8/1995 | Emerson et al. | |
| 5,486,359 | 1/1996 | Caplan et al. | |
| 5,658,756 | 8/1997 | Rodan et al. | 435/69.1 |

FOREIGN PATENT DOCUMENTS

WO 96/05290  2/1996  WIPO.

OTHER PUBLICATIONS

Akatsu et al. J. Bone Miner. Res. vol. 7 (11), pp. 1297–1306, 1992.
Burger et al. J. Exp. Med. vol. 156, pp. 1604–1614, 1982.
Tanaka et al. J. Clin. Invest. vol. 91, pp. 257–263, 1993.
Kurihara et al. Blood, vol. 74 (4), pp. 1295–1302, 1989.
Shioi, A. et al. Calcif Tissue Intl 55 (1994) 387–394.
Gattei, V. et al. J. Cell Biol. 116 (1992) 437–447.
Grano, M. et al. Exp Cell Res. 212 (1994) 209–218.
Billecoca, A. et al. Proc Natl Acad Sci USA 87 (1990) 6470–6474 Aug.
Chambers, T. J. et al. Proc Natl Acad Sci USA 90 (1993) 5578–5582 Jun.
Takahashi, N. et al. Endocrinology 123 (1988) 2600–2602.
Yoneda, T. et al. Endocrinology 129 (1991) 683–689.
Akatsu, T. et al. J. Bone Min. Res. 7 (1992) 1297–1306.
Oursler, M. J. et al. J. Bone Min. Res. 6(1991) 375–385.
Grano, M. et al. J. Bone Min. Res. 9 (1994) 1013–1020.
Prallet, B. et al. J. Bone Min. Res. 7 (1992) 405–414.
Takahashi, N. et al., "Endocrinology," vol. 122(4), pp. 1373–82, 1988.
Suda, T. et al., "Bone," vol. 17(2) (supplement), pp. 87S–91S, Aug. 1995.
Manolagas, S.C. et al., "New England Journal of Med.," vol. 332(5), pp. 305–311, 1995.
Kotake, S. et al., "J. of Bone and Mineral Res.," vol. 11(1), pp. 88–95, 1996.
Kurihara, N. et al., "Endocrinology," vol. 126(5), pp. 2733–2741, 1990.
Wesolowski, G. et al., Experimental Cell Research, vol. 219(2), pp. 679–686, Aug. 1995.
Takahashi, N. et al., J. of Bone and Mineral Research vol. 6(9), pp. 977–985, 1991.
Cirasole, C. et al., Ital. J. Mineral Electrolyte Metab., vol. 8(4), pp. 153–165, Dec. 1994.
Osdody, P. et al., J. of Experimental Zoology, vol. 224, pp. 331–344, 1982.
Shiina–Ishimi, Y. et al., Biochem. & Biophys. Research Comm., vol. 134(1), pp. 400–406, Jan. 1986.
Manolagas, S.C. et al., "The Role of Vitamin D in Bone Marrow Cell Differentiation" from Vitamin D (ed. A.W. Norman et al.), pp. 675–683, 1994.
Zaidi, M. et al., Biol. Rev., vol. 68(2), pp. 197–264, 1993.
Suda, T. et al., Folia Endocrinol. vol. 67(1), pp. 144–155, 1991.
Suda, T. et al., J. Jpn. Orthop. Assoc., vol. 65, pp. 261–270, 1991.
Scheven, B.A.A. et al., Bone & Mineral, vol. 14, pp. 221–235, 1991.
Manolagas, S.C. et al., Seminars in Nephrology, vol. 14(2), pp. 129–143, Mar. 1994.
Butler, W.T., Conn. Tissue Research, vol. 23(2–3), pp. 123–136, 1989.
Abe, E. et al., J. of Bone & Mineral Research, vol. 3(6), pp. 635–645, Dec. 1988.
Van de Wijngaert, F.P. et al., Bone & Mineral, vol. 3, pp. 97–110, 1987.
Chowdhury, M.H. et al., Calcif. Tissue Int., vol. 49(4), pp. 275–279, Oct. 1991.
Hagenaars, C.E. et al., Calcif. Tissue Int., vol. 54(20, pp. 170–174, 1994.
Hentunen, T.A. et al., Biochem. & Biophys. Research Comm., vol. 209(2), pp. 433–443, Apr. 1995.
Flanagan, A.M. et al., Int. J. Exp. Path., vol. 73(3), pp. 387–401, 1992.

Primary Examiner—Leon B. Lankford, Jr.
Assistant Examiner—Christopher R. Tate
Attorney, Agent, or Firm—Joanne M. Giesser; Jack L. Tribble

[57] ABSTRACT

Methods of obtaining enriched populations of osteoclast precursor cells which can be released from tissue culture dishes and used for biochemical studies are described. Osteoblastic cells and bone marrow cells are co-cultured. Next a $\alpha_v\beta_3$ receptor ligand, such as echistatin is used for cell detachment. The result is an 75–95% pure enriched population of tartrate resistant acid phosphatase (TRAP$^+$) cells, in high yields ($2-3 \times 10^6$ cells per experiment) can be obtained. These cells are mostly mononucleated and based on their characteristics are considered to be pre-fusion osteoclasts (pOC cells). The precursor osteoclasts can be reseeded onto osteoblasts to obtain an enriched population of mature, multinucleated osteoclast cells.

6 Claims, No Drawings

METHOD FOR PRODUCING A HIGHLY ENRICHED POPULATION OF OSTEOCLAST CELLS

This is a continuation of application Ser. No. 08/419,210 filed Apr. 10, 1995 now U.S. Pat. No. 5,719,058.

DESCRIPTION OF THE INVENTION

This invention relates to a method of producing a population of cells which is highly enriched in its content of osteoclast precursor cells, and to the cell populations so produced.

BACKGROUND OF THE INVENTION

Osteoclasts are terminally differentiated cells which play a key role in bone resorption. Due to the low number of mammalian osteoclasts and the difficulty to isolate them from bone tissue, and from other cells, their characterization has been limited primarily to immunohistochemistry or anatomical and physiological measurements on single cells.

Several attempts have been made, with limited success, to identify, isolate and establish in culture, cells capable of differentiating into osteoclasts from either bone marrow (Billecocq et al., 1990 *Proc. Nat. Acad. Sci. USA* 87:6470–6474; Prallet et al., 1992, *J. Bone Min. Res.* 7:405–414; and Chambers et al., 1993, *Proc. Nat. Acad. Sci. USA* 90:5578–5582) or leukemic and promyelocytic cell lines (Yoneda et al., 1991, *Endocrinology* 129:683–689; Gattei et al., 1992 *J. Cell Biol.* 116:437–447). Recently, cells obtained from human giant cell tumors of bone were reported to form osteoclasts in culture (Grano et al., 1994 *J. Bone Min. Res.* 9:1013–1020; Grano, et al., 1994 *Exp. Cell Res.* 212:209–218).

To obtain enriched osteoclast preparations, Akatsu et al., 1992, *J. Bone Miner. Res.* 7:1297–1306; cultured the osteoblastic and bone marrow cells on collagen gel-coated dishes, and released the cells from the collagen matrix using collagenase. However, the yield of osteoclastic cells was quite low. Recently, Shioi et al., 1994, *Calcif. Tissue Int.* 55:387–394; using a similar co-culture system reported the enrichment of generated osteoclasts by treating the cultured cells with bacterial collagenase to remove the stromal supporting cells. By this procedure they obtained 60% pure tartrate resistant acid phosphate positive (TRAP$^+$) cells, however the osteoclasts were not available except as attached cells to either dishes or bone slices.

Oursler et al., 1991, *J. Bone Min. Res.* 6:375–385 cultured avian osteoclasts and further purified the osteoclasts by density gradient centrifugation. This method yielded an enriched population of TRAP$^+$ cells capable of bone resorption.

To date, however, the only mammalian osteoclasts obtained in high yields (300,000 per rabbit) and purity (98%) are rabbit osteoclasts (Tezuka et al., 1992, *Biochem. Biophys. Res. Comm.* 186: 911–917). These cells, however were attached to the plastic culture dishes and cannot be removed.

DESCRIPTION OF THE INVENTION

This invention relates to a method of obtaining a highly enriched population of osteoclast precursor cells comprising co-cultivation of osteoblastic cells and bone marrow cells and treatment of the culture with an integrin $\alpha_v\beta_3$ receptor ligand to release a population which is highly enriched with precursor osteoclasts. This invention also comprises the process of obtaining a highly enriched population of mature osteoclast cells comprising reseeding the population of highly enriched precursor osteoclast cells so produced on osteoblast cells for a time sufficient for the osteoclast precursor cells to fuse into mature multinucleated osteoclasts.

This invention also relates to the enriched populations of mammalian precursor osteoclasts. Yet another aspect of this invention is a population which is highly enriched with mature osteoclasts. Further aspects of this invention is a suspension culture comprising mammalian osteoclast precursor cells, and to suspension cultures comprising mature osteoclast cells.

A further aspect of this invention is an assay for bone resorption activity comprising exposing a population of mammalian cells which is highly enriched in osteoclasts, but also comprising osteoblasts, to a bone, in the presence of Vitamin D3 or a biologically active derivative of Vitamin D3 and measuring the bone-resorption which occurs.

In accordance with this invention, it was observed that integrin $\alpha_v\beta_3$ receptor ligands appear to play a role in cell attachment and in the fusion of the precursor osteoclasts into multinucleated osteoclastic cells in the bone marrow co-culture system. One aspect of this invention thus uses $\alpha_v\beta_3$ receptor ligands to isolate a highly enriched population of pre-fusion cells. The pre-fusion cells (also referred to as precursor osteoclasts) can be co-cultured with osteoblasts so that they differentiate into mature osteoclasts. This invention also relates to the enriched populations of precursor osteoclasts and mature osteoclasts produced by the processes described above.

As used throughout the specification and claims, the following definitions will apply:

"$\alpha_v\beta_3$ receptor ligand" is any molecule which binds to the $\alpha_v\beta_3$ receptor. An $\alpha_v\beta_3$ receptor ligand can be identified by determining whether it replaces echistatin which has bound to the $\alpha_v\beta_3$ receptor in a competitive binding assay. Those compounds which replace echistatin are considered $\alpha_v\beta_3$ receptor ligands. Examples of $\alpha_v\beta_3$ receptor ligands include RGD-containing pepetides and non-peptides which bind to the same receptor as RGD-peptides.

"highly enriched" means that a population of cells contains at least about 75% of a single type of cell, more preferably at least about 90%, and more preferably at least about 95% of a particular cell type.

"biologically active derivative of Vitamin D3" refers to any metabolite of Vitamin D3 which is normally produced by a mammal and contributes to bone metabolism. Examples include 25-hydroxy Vitamin D3, and 1,25-dihydroxy Vitamin D3.

"precursor osteoclasts" are pre-fusion osteoclast cells. Precursor osteoclast cells are characterized by their ability to generate bone-resorbing, giant, multi-nucleated osteoclasts within about 24 hours of being plated on osteoblasts. Like mature multi-nucleated osteoclasts, they may also be defined by the following characteristics: they are TRAP$^+$; have calcitonin (CT) receptors; express $\alpha_v\beta_3$ integrin; have osteopontin (OP); carbonic anhydrase II (CAII). The precursor osteoclasts made according to the processes of this invention also form pits when plated on bone slices along with osteoblasts in the presence of Vitamin D3 or a biologically active derivative of Vitamin D3.

"suspension culture" means any culture containing precursor osteoclasts or mature osteoclasts which are not attached to the culture vessel.

Any $\alpha_v\beta_3$ receptor ligand may be used in accordance with this invention. Known $\alpha_v\beta_3$ receptor ligands include vitronectin, echistatin, kirstin, other snake venoms, other RGD-containing peptides, and non-peptides which bind to same receptor as RGD-containing peptides. One preferred $\alpha_v\beta_3$ receptor ligand is echistatin. Echistatin is an RGD-containing snake venom which inhibits osteoclast attachment and formation (Sato, et al., 1990 *J. Cell Biol.* 111:1713–1723; Tanaka, et al., 1991, *J. Bone Min. Res.* 6:S148 both of which are hereby incorporated by reference.).

One aspect of this invention is a convienent procedure to obtain a suspension culture of abundant, highly enriched precursor osteoclast cells which (except for their mono-nucleated characteristic) have all the characteristics of mature multinucleated osteoclasts. The cultures of this invention comprise a population of cells, at least about 75% of which are precursor osteoclasts. In a preferred embodiment, the population comprises at least about 90% precursor osteoclasts, and in particularly preferred embodiments, the population contains at least about 95% precursor osteoclasts. One important distinguishing feature of this invention is that the precursor osteoclasts of the population are in a suspension, i.e. they are not attached to a plastic or glass substrate, and are thus able to be further manipulated by the researcher. This invention thus makes it possible to study the biochemistry of osteoclasts, the regulation of genes expressed by these cells and other characteristics.

The culture processes of this invention can be used with any species of animal cells which can form osteoclasts, and are able to be cultured in vitro. Preferred animals include mammals, particularly those of bovines, rodents (such as mouse and rat), and primates (such as human and monkey). Particularly preferred are human, and mammalian species such as rat and mouse or other animals whose osteoclasts share biochemical characteristics with human osteoclasts.

This invention includes the first detailed characterization of the properties of mononuclear cells which can generate multinucleted osteoclasts within 24 hours in culture. While not wishing to be bound by theory, since the cells of this invention have all the properties tested so far which are attributed to highly differentiated osteoclasts, it is believed that precursor osteoclast cells represent a stage of differentiation in the osteoclast lineage cells just prior to fusion, which is the last step in osteoclast differentiation.

In accordance with this invention, bone marrow and osteoblast cells are co-cultured according to known techniques, and using known and available cell lines. For example, one mouse osteoblast cell line which may be used is MB1.8 (a mouse calvaria-derived osteoblastic cell line), but any other cell line which supports osteoclastogenesis may also be employed, including ST-2 (a publicly available line), other calvaria-derived osteoblastic stromal cell lines, or primary osteoblast cell lines.

Co-culture of bone marrow and osteoblast cells should continue for approximately 6 days (depending on the particular cell lines used) or until the cell lines have yielded the maximum amount of pre-fusion osteoclast cells. However, if cells are cultured too long, multinucleated osteoclasts will form which, due to their attachment to the cell culture plate, cannot be used in this invention. Prior to the formation of giant multi-nucleated osteoclasts, the majority of cells of the osteoblast cell line should be detached from the co-cultured bone marrow cells using an enzyme system which disrupts the co-culture, such as dispase/collagenase. The amounts of enzymes may vary with the specifc enzyme used and the specific activity, but should be sufficient to break up the attachment of osteoblasts to precursor osteoclasts. Generally, approximately 1 mg/ml of each enzyme is sufficient.

Next, the remaining cells are treated with the $\alpha_v\beta_3$ receptor ligand for a time and an amount sufficent to inhibit the formation of multinucleated osteoclastic cells in the co-culture system as well as to inhibit the attachment and function of multi-nucleated osteoclasts themselves. In a preferred embodiment of this step, the remaining cells were treated with 10 to 50 nM echistatin for at least about 10 minutes. In a particularly preferred embodiment, approximately 30 nM of echistatin is used for approximately 20 minutes.

Cells isolated from bone marrow co-cultures by treatment with the $\alpha_v\beta_3$ receptor ligand attach to coverslips or tissue culture wells within one hour. This isolated population of cells is well-defined: based on their $TRAP^+$ staining and their ability to form mature osteoclasts when seeded back on osteoblasts, these cells were identified as precursor osteoclasts (pOC cells). Seventy-five to ninety per cent of the cells are mononuclear; the rest are multinucleated cells with two to four nuclei. Almost all the cells (88–95%) are $TRAP^+$. A few $TRAP^+$ cells, (approximately 2–3%) may still be attached to alkaline phosphatase-positive mononuclear cells, presumably osteoblastic cells. A small number of cells which (approximately 3–4%) do not stain for either TRAP or alkaline phosphatase may also be present.

Another feature of this invention is that a high yield of cells is possible. For example, yields of about 150,000 cells per 150 $cm^2$ tissue culture dish, or approximately 1000 cells/$cm^2$ are common.

To further characterize the precursor osteoclast cells so produced, various assays were performed on the highly enriched population. Since the presence of abundant calcitonin receptors is regarded as a distinctive marker of the osteoclast phenotype, the pOC cells were examined for this property according to known techniques. The osteoclast precursors bound a large number of salmon calcitonin ($^{125}$I-sCT) molecules, as visualized by autoradiography, and binding was displaced by a 100 fold excess of unlabeled sCT. However, some $TRAP^+$ cells did not bind calcitonin.

Exposure to salmon calcitonin (sCT) for 10 minutes increased cAMP in pOC cells in a dose-dependent manner, up to 250 fold at 10 nM sCT, while $PGE_2$ had a small stimulatory effect and PTH was without effect.

The isolated pOC cells, when plated onto 1,25-dihydroxy $D_3$-treated osteoblast cells fuse rapidly (within 24 hours) to form multinucleated TRAP+osteoclast-like cells. The pOC cells which are kept frozen in liquid nitrogen and thawed, retain the capability to form multinucleated TRAP+cells.

The pOC cells possess other features of multinucleated osteoclasts. On slices of steer cortical bone, and in the presence of osteoblasts and Vitamin D3 or a biologically active derivative of Vitamin D3, the pOC cells formed pits after 24 hours of incubation and this activity was inhibited by calcitonin. The resorption pits were heterogenous in size, varying from single to composite pits. The resorption pits coincided with intense F-actin staining. The actin rings could be visualized as early as 2 hours after the pOC cells are plated on bone slices.

In accordance with this invention, the pOC cells resorb bone only in the presence of osteoblastic cells and 1,25-dihydroxy vitamin $D_3$. It was also found that the number of pits as well as the number of F-action rings not only correlate with each other, but both increase proportionately when pOC cells are co-cultured with an increasing number of osteoblast cells. There were no F-action rings when pOC cells were cultured in the absence of osteoblastic cells or a Vitamin $D_3$ derivative.

The pOC cells express mRNAs for proteins found in multinucleated osteoclasts. For example, high mRNA levels for $\alpha_v$ (7.0 kb) and $\beta_3$ (6.5) integrin subunits, calcitonin receptor (4.2 kb), carbonic anhydrase II (1.8 kb) and osteopontin (1.8 kb) can be observed. In addition, they express mRNA for protein tyrosine phosphatase $\epsilon$ (a major transcript of about 5 kb and a minor transcript of about 3 kb), OC-2 (1.8 kb), a possible cysteine proteinase, and matrix metallo-proteinase 9 or 92 kD type IV collagenase (3.0 kb). All of these mRNAs are known to be highly or preferentially expressed in osteoclasts. These findings illustrate the use of pOC cells produced according to this invention for identifying and studying osteoclast-associated proteins.

Isolated osteoclasts as well as multinucleated osteoclasts derived from the in vitro co-cultures express high levels of $pp60^{c-src}$. pOC cell lysates immunoprecipitated with the monoclonal antibody mAB 327, which recognizes c-src 60 kDa protein, and immunoblotted with phosphotyrosine antibodies, show an abundance of phosphorylated $pp60^{c-src}$.

The highly enriched population of pOC cells can then be reseeded onto osteoblast cells in order for the pOC cells to differentiate into multinucleated osteoclasts. The osteoblastic cells may be the same as used in the co-culture process, or may be a different osteoblast line. An example of a suitable osteoblast line is the murine MB1.8 line which has been treated with 1,25-dihydroxy-vitamin $D_3$. Other appropriate lines include: bone marrow stromal lines, primary osteoblast cells lines from calvaria or any other cell line which supports osteoclast formation. Upon plating, the pOC cells fuse within a short period of time, generally within 24 hours, to form multinucleated, $TRAP^+$ osteoclasts.

Another aspect of this invention is an assay for the bone resorption inhibitory or stimulatory effect of a test substance comprising placing an osteoclast-enriched population of cells which also comprises osteoblasts on a bone slice, in the presence of Vitamin D3 or a biologically active derivative thereof, and a test substance (which may contain a putative inhibitory substance or a putative stimulatory substance) and measuring the amount of bone resorption, by, e.g., determining the number of pits formed. The resulting activity can be compared to the activity of a control where no test substance was present. Thus a further aspect of this invention is a method of identifying a drug which inhibits bone resorption comprising placing an osteoclast-enriched population of cells which also comprises osteoblasts on a bone slice in the presence of Vitamin $D_3$ or a biologically active derivative thereof, and a putative drug having bone resorption inhibitory activity, and determining whether resorption occurs. This invention also includes bone resorption- inhibiting drugs identified by this method.

The following non-limiting Examples are presented to better illustrate the invention.

EXAMPLE 1

Co-Culture And Isolation of Pre-Fusion Cells

Mouse bone marrow-osteoblast co-culture system was performed essentially as described by Takahashi et al., 1988 *Endocrinology* 123:2600–2602, which is hereby incorporated by reference. A cell line (MB1.8), (Tanaka et al., 1992 *J. Bone Min. Res.* 7:S307) established from neonatal mouse calvaria was found to support bone marrow cell differentiation into osteoclasts. MB1.8 cells were plated at 10,000/cm² in Alpha Modification of Minimal Eagle's Medium ($\alpha$-MEM) containing 10% fetal bovine serum and 10 nM $1,25(OH)_2D_3$. (Fetal Bovine Serum was from JRH Biosciences, Lenexa, Kans. Other tissue culture reagents, were from Gibco/BRL Life Technologies, Inc., Grand Island, N.Y.)

Balb/C male mice (six weeks old) were sacrificed under $CO_2$, and tibiae and femora were aseptically removed. The bone ends were cut off with scissors and the marrow cavity was flushed with 1 ml $\alpha$-MEM by using a 27 G needle. The bone marrow cells were then filtered through 70 mm nylon mesh. Cells were centrifuged for 7 minutes at 300×g and washed once with $\alpha$-MEM and finally resuspended and aliquoted at 25,000 cells/cm² onto the MB1.8 cultures. Medium was replaced every two days.

After 6 days, many mononuclear and some multinuclear TRAP+ cells were present in these cultures. Cultures were washed twice with PBS and treated with collagenase/dispase (1 mg/ml each in PBS) at 37° C. for 20 minutes. (Collagenase Cat. # 034-10533 was from Wako Chemicals USA, Inc., Dallas, Tex. Dispase Cat. # 165859 was from Boehringer Mannheim Corp., Indianapolis, Ind.) Released cells, mostly osteoblasts, were removed with a pipet and the plates were washed three times with PBS. The remaining cells were incubated with 30 nM echistatin in $\alpha$-MEM containing 1% BSA for 20 minutes at 37° C. These cells were collected, pelleted and washed once with $\alpha$-MEM containing 10% FBS and were plated either on bone, coverslips or in wells, as indicated below.

TABLE 1

Abundance of $TRAP^+$ cells in enriched populations of pOC cells

| Experiment number | $TRAP^+$ cells | $TRAP^-$ Cells |
|---|---|---|
| 1 | 829 (94%) | 48 (6%) |
| 2 | 614 (88%) | 81 (12%) |
| 3 | 1006 (91%) | 102 (9%) |

Freshly isolated pOCs were plated at 12,500 cells/cm² on serum coated wells and allowed to attach for 2 hrs. Cells were fixed and stained for TRAP and in some experiments counterstained for alkaline phosphatase as described. Approximately 1,000 cells were counted per well.

EXAMPLE 2

Characterization of pOC Cells

Measurement of cAMP: Osteoclast precursors were isolated as described in Example 1 and plated at 240,000 cells per well in 24 well dishes that were precoated with FBS. Cells were allowed to attach for 90 minutes, washed twice with $\alpha$-MEM and treated with 1 mM isobutylmethylxanthine (IBMX) for 10 minutes at 37° C. Bovine parathyroid hormone (PTH), salmon calcitonin (sCT), or $PGE_2$ were added at the indicated concentrations and the cultures were incubated for 10 minutes at 37° C. (Bovine PTH 1–34 was from Bachem, Inc., Torrance, Calif. Salmon calcitonin was from Peninsula Laboratories, Belmont, Calif. The IBMX and TRAP kit were from Sigma, St. Louis, Mo.).

The medium was aspirated and the cells were extracted three times with absolute ethanol. The extracts were evaporated to dryness and analyzed for cAMP by radioimmunoassay according to the manufacturer's instructions (Amersham Corp.).

TABLE 2

Effects of CT, PTH and PGE$_2$ on cAMP accumulation in pOC cells.

| | Additions | cAMP (pmol/10$^5$ cells) |
|---|---|---|
| Experiment 1 | none | 0.29 ± 0.026 |
| | sCT(10$^{-11}$M) | 6.81 ± 1.14* |
| | sCT (10$^{-8}$M) | 70.8 ± 5.1* |
| Experiment 2 | none | 0.15 ± 0.025 |
| | sCT (10$^{-8}$M) | 36.9 ± 2.5* |
| | PTH (10$^{-7}$M) | 0.19 ± 0.027 |
| | PGE$_2$ (10$^{-6}$M) | 0.27 ± 0.008* |

Freshly isolated pOCs were plated on serum coated 24-well culture dishes at 120,000 cells/cm$^2$ (Exp. 1) or 65,000 cells/cm$^2$ (Exp. 2) and allowed to attach for 2 hours. Cultures were washed and pretreated for 10 mins at 37° C. with 1 mM IBMX. Cells were then incubated for 10 mins with sCT, PTH or PGE$_2$ at 37° C. The medium was aspirated and cAMP was extracted 3× with ethanol. The extracts were analyzed for cAMP by radioimmunoassay as described. Results given in Table 2, above are the mean±s.d. for triplicate wells. The asterisk signifies that the amount was significantly greater than control group, p<0.001.

Calcitonin Autoradiography

Isolated osteoclast precursors from Example 1 were plated on coverslips that were precoated with FBS for two hours at 37° C. The cells were incubated for one hour at room temperature in α-MEM containing 0.1% BSA and 0.3 nM $^{125}$I-sCT with or without 100 fold excess unlabeled sCT. ($^{125}$I-salmon calcitonin (2000 Ci/mmol) was purchased from Amersham Corp., Arlington Heights, Ill.)

Cultures were washed five times with ice cold α-MEM, fixed in 10% formalin for 10 minutes at room temperature and permeabilized with ethanol/acetone (1:1) for 2 minutes and stained for TRAP. Coverslips were mounted on slides, dipped in ILFORD K.2 emulsion (Polysciences, Warrington, Pa.) diluted 2 parts emulsion:1 part 6% glycerol, dried and stored at 4° C. for 2 weeks. Slides were developed in Kodak D-19 developer diluted 1:1 with water for 5 minutes followed by fixer for 5 minutes, washed with deionized water for 15 minutes and air dried.

RNA Isolation and Northern Blot Analysis

Total cellular RNA was isolated by guanidinium isothiocyanate and phenol extraction as described in Chomczynski, P et al., 1987 Anal. Biochem. 162:156–159, which is hereby incorporated by reference. Total RNA (25 μg) was electrophoresed through 1% agarose-formaldehyde gels and electroblotted onto nylon filters (Hybond-N, Amersham Corp., Arlington Heights, Ill.). Blots were prehybridized in buffer containing 50% formamide, 5×SSC (1×SSC=0.15M NaCl, 0.015M sodium citrate), 5×Denhardt's solution and 100 μg/ml sonicated salmon sperm DNA and hybridized at 42° C. in fresh buffer containing the indicated cDNAs which were labeled with a random primer DNA labeling kit (Pharmacia Biotech Inc., Piscataway, N.J.) using [α-$^{32}$P-dCTP] (Amersham Corp.). Blots were washed with 0.1× SSC/0.1% SDS at 65° C. for 30 minutes and exposed to Kodak XAR film. The cDNA clones were generated for MMP-9, OC-2, and osteopontin by using cDNA libraries of rabbit osteoclasts (Tezuka et al., 1992, Biochem. Biophys. Res. Comm. 186: 911–917; 1994 J. Biol. Chem 269: 15006–15009; and 1994 J. Biol. Chem. 269: 1106–1109 each of which is hereby incorporated by reference). PTP ε was cloned from mouse osteoclastic cells (Schmidt et al., 1993, J. Bone Min. Res. 8:S144, which is hereby incorporated by reference). The following cDNA probes were cloned by PCR based on the reported sequences: human a$_v$ (Suzuki et al., 1987 J. Biol. Chem. 262:14080–14085, which is hereby incorporated by reference; mouse calcitonin receptor (Lin et al., 1991 Science 254:1022–1024, which is hereby incorporated by reference); and human β$_3$ (Frachet et al., 1990 Molec. Bio. Rep. 14:27–33, which is hereby incorporated by reference). mAB 327 which recognizes pp60$^{c-src}$ was a gift of Dr. J. Brugge (Lipsich, et al., 1983 J. Virology 48:352–360,which is hereby incorporated by reference).

Measurement of Bone Resorption

Bone slices (20 mm$^2$) were prepared from bovine cortical bone by a low speed diamond saw (Buehler, Lake Bluff, Ill.). Slices were cleaned by ultrasonication (Branson, Shelton, Conn.) in distilled water (15 mins) three times, rinsed in distilled water and placed in 96-well culture plates (Costar Co., Cambridge, Mass.). The bone slices were sterilized under UV light. Bone slices were rehydrated with medium 199 containing 10% FBS and penicillin/streptomycin solution. A suspension (20,000 cells) of the TRAP+ bone marrow cells were added to each well with or without MB1.8 cells in the presence or absence 10 nM 1,25-dihydroxy-Vitamin D$_3$, or in the presence or absence of MB1.8 cells pre-treated for 48 hours or not with 1,25-dihydroxy Vitamin D$_3$ (1,25(OH$_2$)D$_3$). After 24 hrs, the bone slices are fixed and stained with 1% toluidine blue as described previously (Demster, et al., 1987 J. Bone Min. Res. 2:443–448; 1987.). Results are given in TABLE 3, below.

TABLE 3

Effects of osteoblastic cells and 1,25-dihydroxy - Vitamin D$_3$ on bone resorption by pOC cells

| | Number of pits/bone slice | |
|---|---|---|
| Culture Conditions | Experiment 1 | Experiment 2 |
| pOC cells | 0 | 0 |
| +1,25 (OH)$_2$D$_3$ | 0 | 1 |
| +MB1.8 cells | ND | 1 |
| +MB1.8 cells+1,25(OH)$_2$D$_3$ | ND | 56 ± 20 |
| Pretreated with 1,25(OH)$_2$D$_3$: | | |
| +MB1.8 cells | 178 ± 59 | 57 ± 40 |
| +MB1.8 cells+1,25(OH)$_2$D$_3$ | 387 ± 60 | 196 ± 68 |

ND = not determined

Immunofluorescence Microscopy

Bone slices containing the pOC cells in the presence or absence of MB1.8 cells or 1,25-dihydroxy Vitamin D$_3$ (under the same conditions as described above for measurement of bone resorption) were fixed in 3% paraformaldehyde, 2% sucrose in PBS for 5 min at room temperature. The cells were permeabilized in 0.5% Triton X-100 for 5 min on ice. F-actin was stained with rhodamine-conjugated phalloidin (Molecular Probes, Inc.), 5 U/ml for 15 min at room temperature.

Immunoprecipitation and Immunoblots

The pOC cells from Example 1 were allowed to attach to dishes for 3 hours and lysed in RIPA buffer (150 mM NaCl, 10 mM Tris, 1% Triton X-100, 1% deoxycholate, 1 mM EDTA, 1 mM sodium orthovanadate, 10 mg/ml leupeptin, 1 TIU/ml aprotinin, and 1 mM PMSF, pH 7.3) 100 μl/100,000 cells. The lysate was preincubated with sepharose 4B-200 for 1 hr at 4° C., then divided into 2 aliquots. One was incubated with 2 μl pp60$^{c-src}$ antibody (mAb327) overnight at 4° C., the other was left untreated. The lysates were reacted with goat-anti-mouse sepharose for 1 hr at 4° C., the beads were washed 5 times with RIPA buffer, then treated with Laemmli sample buffer for 3 minutes at 95° C. and run on a 10% SDS polyacrylamide gel (Laemmli, 1970 *Nature* 227:680–685, which is hereby incorporated by reference). The proteins were electro-transferred to Immobilon P overnight, the membrane was blocked in 100 mM NaCl, 10 mM Tris, 0.1% Tween, 1% BSA, incubated with anti-phophotyrosine antibody horseradish peroxidase conjugate RC2OH (Transduction Laboratories, Lexington, Ky.) diluted 1:10,000, washed extensively, reacted with ECL reagents (Amersham) and exposed to XAR5 film (Kodak). Each lane contained protein from 100,000 cells.

What is claimed is:

1. A method of producing a cell population which is highly enriched with mature mammalian osteoclast cells wherein said population is derived from precursor osteoclast cells which are TRAP$^+$, comprising:

(a) co-cultivating bone marrow cells and osteoblast cells;

(b) treating the co-cultivated cells with an $\alpha_v\beta_3$ receptor ligand to produce a precursor osteoclast enriched population; and (c) reseeding the precursor osteoclast enriched population on osteoblastic cells for a time sufficient for mature osteoclast cells to form.

2. The method according to claim 1 wherein the $\alpha_v\beta_3$ receptor antagonist is echistatin.

3. A population of cells highly enriched in mammalian osteoclasts wherein said population is derived from precursor osteoclast cells which are TRAP$^+$, comprising:

(a) co-cultivating bone marrow cells and osteoblast cells;

(b) treating the co-cultivated cells with an $\alpha_v\beta_3$ receptor ligand to produce a precursor osteoclast enriched population; and (c) reseeding the precursor osteoclast enriched population on osteoblastic cells for a time sufficient for mature osteoclast cells to form.

4. The population of cells according to claim 3 which are selected from the group consisting of human, mouse and rat cells.

5. A suspension culture comprising a population highly enriched of mature mammalian osteoclast cells wherein said population is derived from precursor osteoclast cells which are TRAP$^+$, produced by a process comprising:

(a) co-cultivating bone marrow cells and osteoblast cells;

(b) treating the co-cultivated cells with an $\alpha_v\beta_3$ receptor ligand to produce a precursor osteoclast enriched population; and (c) reseeding the precursor osteoclast enriched population on osteoblastic cells for a time sufficient for mature osteoclast cells to form.

6. The culture according to claim 5 which is selected from the group consisting of human, mouse and rat.

* * * * *